US011459301B2

(12) United States Patent
Shan

(10) Patent No.: US 11,459,301 B2
(45) Date of Patent: Oct. 4, 2022

(54) CRYSTALLINE FORM OF S-APOMORPHINE

(71) Applicant: ACLIPSE ONE, INC., Radnor, PA (US)

(72) Inventor: Ning Shan, Chandler, AZ (US)

(73) Assignee: Aclipse One, Inc., Radnor, PA (US)

( * ) Notice: Subject to any disclaimer, the term of this patent is extended or adjusted under 35 U.S.C. 154(b) by 98 days.

(21) Appl. No.: 17/054,853

(22) PCT Filed: May 13, 2019

(86) PCT No.: PCT/US2019/032026
§ 371 (c)(1),
(2) Date: Nov. 12, 2020

(87) PCT Pub. No.: WO2019/222103
PCT Pub. Date: Nov. 21, 2019

(65) Prior Publication Data
US 2021/0214310 A1    Jul. 15, 2021

Related U.S. Application Data

(60) Provisional application No. 62/670,822, filed on May 13, 2018.

(51) Int. Cl.
*C07D 221/18* (2006.01)
*A61P 25/28* (2006.01)

(52) U.S. Cl.
CPC ........ *C07D 221/18* (2013.01); *C07B 2200/13* (2013.01)

(58) Field of Classification Search
CPC ... C07D 221/18; C07B 2200/13; A61P 25/28; Y02P 20/54
See application file for complete search history.

(56) References Cited

PUBLICATIONS

Mead, R. J., "S [+] Apomorphine is a CNS penetrating activator of the Nrf2-ARE pathway with activity in mouse and patient fibroblast models of amyotrophic lateral sclerosis." Free Radical Biology and Medicine 61 (2013): 438-452.*
Cleveland Clinic Amyotrophic Lateral Sclerosis (ALS) 2021 (https://my.clevelandclinic.org/health/diseases/16729-amyotrophic-lateral-sclerosis-als#:~:text=Can%20ALS%20be%20prevented%3F,further%20understanding%20of%20the%20disease), (p. 1-20).*
Verweij, M. F., Preventive medicine between obligation and aspiration. vol. 4. Springer Science & Business Media, 2013.*
Shekunov, B., "Crystallization processes in pharmaceutical technology and drug delivery design." Journal of crystal growth 211.1-4 (2000): 122-136.*
Saari, W. S., "Synthesis and biological activity of (6aS)-10,11-dihydroxyaporphine, the optical antipode of apomorphine." Journal of Medicinal Chemistry 16.2 (1973): 171-172.*
Supplementary European Search Report, dated Dec. 14, 2021, for European Application Serial No. 19803797.
Reilly et al., Report on the sixth blind test of organic crystal structure prediction methods. Acta Cryst., B72, pp. 439-159 (2016).
Caira et al., Crystalline polymorphism of organic compounds II topics in current chemistry. Springer, Berlin, DE, vol. 198, pp. 163-208 (1998).
Johnston et al., Development and validation of a high-content screening assay to identify inhibitors of cytoplasmic dynein-mediated transport of glucocorticoid receptor to the nucleus. Assay and Drug Development Technologies, vol. 10, pp. 432-456 (2012).
Lehmann et al., Stereoisomers of apomorphine differ in affinity and intrinsic activity at presynaptic dopamine receptors modulating [3H]dopamine and [3H]acetylchol ine release in slices of cat caudate. European Journal of Pharmacology, vol. 88, pp. 81-88 (1983).
Thomas, et al., Kinetic characterization of ebselen, chelerythrine and apomorphine as glutaminase inhibitors. Biochemical and Biophysical Research Communications, vol. 438, pp. 243-248 (2013).
Kitson et al., Application of the Bischler-Napieralski-Pschorr radiosynthesis of (R)-(-)-[6a-14C]apomorphine, a non-selective D1/D2 dopamine recept or agonist. Journal of Labelled Compounds and Radiopharmaceuticals, vol. 49, pp. 517-531 (2006).
International Search Report and Written Opinion for International Application No. PCT/US2019/032026 filed on May 13, 2019.

* cited by examiner

*Primary Examiner* — John M Mauro
(74) *Attorney, Agent, or Firm* — K&L Gates LLP; Louis C. Cullman; Michelle Glasky Bergman

(57) ABSTRACT

The invention is directed to a novel crystalline S-apomorphine hydrochloride hydrate salt.

18 Claims, 3 Drawing Sheets

CRYSTALLINE FORM OF S-APOMORPHINE

CROSS REFERENCE TO RELATED APPLICATIONS

Figure 1:
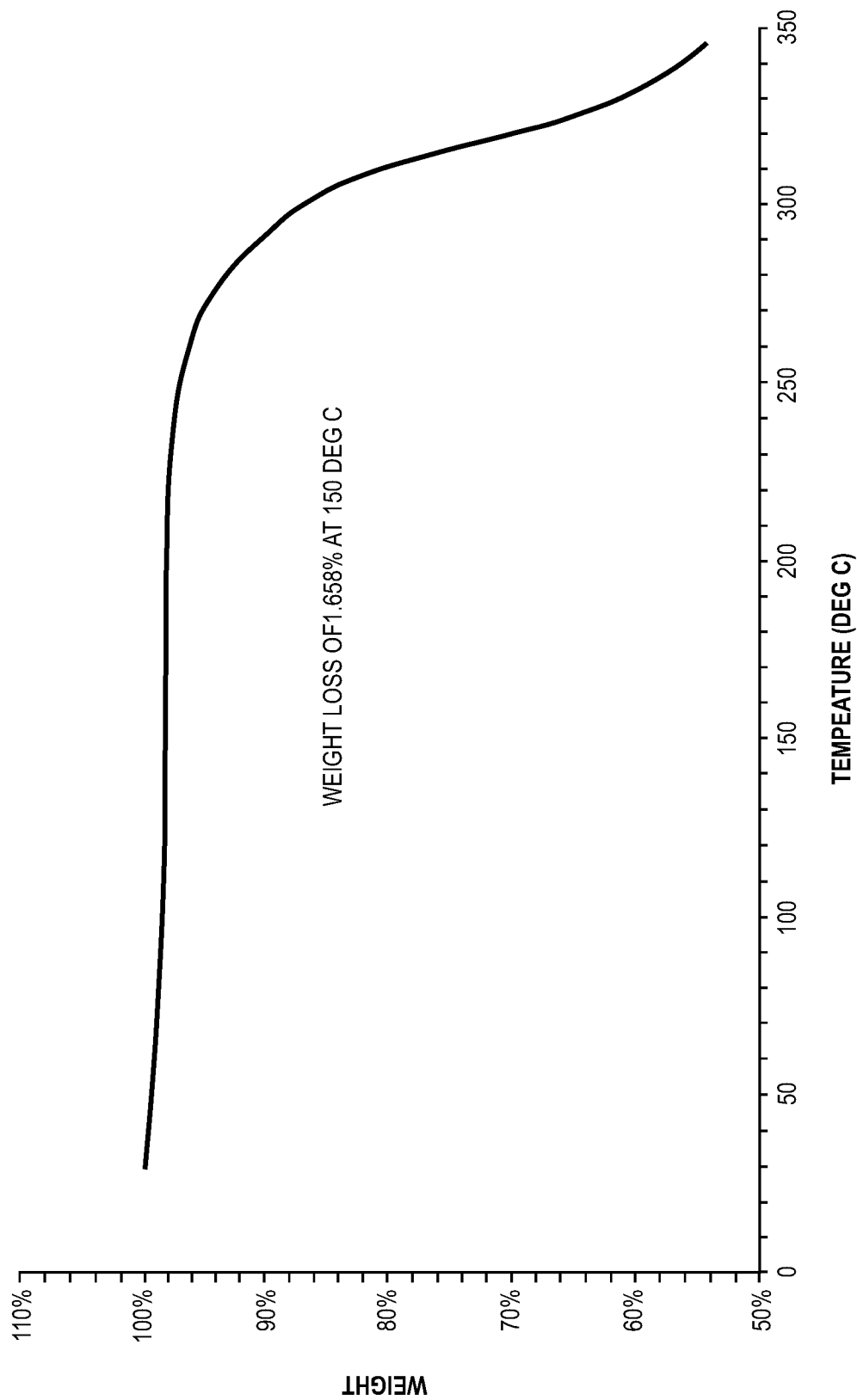

This application is a national phase application based on PCT/US2019/032026 filed on May 13, 2019 which claims priority to U.S. provisional patent application 62/670,822 filed on May 13, 2018, the entire disclosures of which are incorporated by reference herein.

FIELD OF THE INVENTION

The present invention relates to a novel hydrochloride hydrate salt of S-apomorphine and pharmaceutical compositions comprising the same. The S-apomorphine compositions can be used for the safe and effective treatment of human diseases including Amyotrophic Lateral Sclerosis. Such a crystalline material can be used to prepare a solid dosage form, a semi-solid dosage form, or a liquid dosage form in pharmaceutical compositions in a variety of drug delivery systems. Those dosage forms are useful in the prevention and/or treatment of a neurodegenerative or movement disorder, or a condition associated therewith.

BACKGROUND OF THE INVENTION

Active pharmaceutical ingredients (APIs) in pharmaceutical compositions can be prepared in a variety of different chemical forms including chemical derivatives, solvates, hydrates, cocrystals and/or salts. Such compounds can also be prepared in different physical forms of the same chemical composition. For example, they may be amorphous, may have different crystalline forms (polymorphs), and/or may exist in different solvated or hydrated states with no change in the chemical composition of the original API.

The discovery of new salts of a pharmaceutically useful compound provides an opportunity to improve the physicochemical characteristics and subsequently the clinical performance of such a compound. Additionally, it expands the array of resources available for designing, for example, a pharmaceutical dosage form of an API with a targeted/sustained release profile, improved shelf life due to higher physical stability, improved particle size or size distribution, or powder flowability and handling for easier downstream processing including but not limited to changing its route of delivery. For example, crystalline forms of the same chemical composition (polymorphs) can have different aqueous solubilities from one another, where typically the more thermodynamically stable the polymorph is, the less soluble it becomes.

In addition, polymorphs of an API can also differ in physicochemical properties such as solid phase stability and longer shelf-life, different half-life in vivo, higher bioavailability, particle morphology, vapor pressure, density, color, melting point and compressibility. However, it is sometimes difficult to produce the desired polymorph consistently or there is little improvement in their aqueous solubility or characterizing of all polymorphic forms can be challenging. In addition, if only one polymorph is discovered then there is less opportunity to manipulate and improve physicochemical properties of the API. These limitations can adversely affect the API formulation becoming a usable dosage form or even force pharmaceutical companies to abandon the development of an API.

Therefore, it would be highly appreciable to generate novel salts, such as non-solvated salts, solvated salt salts, or mixes thereof, that can address such limitations and enhance the properties of an API such as aqueous solubility, rate of dissolution, bioavailability, $C_{max}$, $T_{max}$, half-life, solid phase stability, shelf life, downstream processability (e.g. flowability, compressibility, degree of brittleness, particle size and size distribution), crystallization of amorphous compounds, decrease polymorphic form diversity, reduce toxicity, taste masking, and/or its production and manufacturing method efficiency. For oral delivery of solid dosage forms, it is frequently advantageous to have novel crystalline molecular complexes of drug materials that possess such improved properties and in particular, increase aqueous solubility and solid phase stability. It is also desirable in general to increase the dissolution rate of such solid forms, increase bioavailability, and provide a more rapid onset to quicken the therapeutic effect. In addition, it is useful to have a crystal form which, when administered to a subject, reaches a peak plasma level faster and has a longer lasting therapeutic plasma concentration, when compared to other existing forms on a dose for dose basis.

S-apomorphine is a weak dopamine antagonist for the treatment of neurological disorders. S-apomorphine, also known as S-(+)-10,11-dihydroxyaporphine or (S)-(+)-apomorphine, is depicted by the following chemical structure:

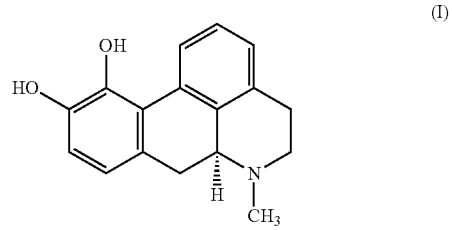 [SMILES: CN1CCc2cccc3c2[C@@H]1Cc1ccc(O)c(O)c1-3]

(I)

Because of the limitations related to the physicochemical properties of S-apomorphine, there is a need to develop novel salts that have improved physicochemical properties including solid form stability, aqueous solubility, and in vivo permeability. Those novel salts can be formulated for use in oral administration to achieve faster onset or possibly improve its clinical profile. It is possible to tackle these limitations by generating novel salts of S-apomorphine, including but not limited to non-solvates and solvates (e.g. hydrates and mixed solvates as well as solvates of salts), and mixtures of thereof, that can modify the rate of dissolution and optimize the clinical pharmacokinetics and efficacy of the drug. These novel salts could be used in the development of novel dosage forms of S-apomorphine.

SUMMARY OF THE INVENTION

The present invention relates to a novel crystalline hydrochloride hydrate salt of S-apomorphine as well as pharmaceutical compositions and pharmaceutical dosage forms comprising hydrochloride hydrate salt. In some embodiments, the hydrochloride hydrate salt has improved solubility, stability, oral bioavailability, and/or safety profile, as compared to S-apomorphine free form. In addition, the disclosure further includes methods for the preparation of the S-apomorphine hydrochloride hydrate salt, pharmaceutical compositions and pharmaceutical dosage forms comprising the S-apomorphine hydrochloride hydrate salt. One aspect of the present invention provides for a crystalline S-apomorphine hydrochloride hydrate salt.

In another embodiment, the salt has a molar ratio of S-apomorphine cation:hydrochloride anion:water that is about 1:1:0.30-0.55.

In another embodiment, the S-apomorphine hydrochloride hydrate salt has a water content of about 1.75-3.2%.

In another embodiment, the S-apomorphine hydrochloride hydrate salt is a S-apomorphine hydrochloride hemihydrate salt.

In another embodiment, the salt of S-apomorphine is characterized by a powder X-ray diffraction pattern comprising any one or more peaks at about 7.99, 8.81, 10.17, 11.00, 11.60, 13.39, 15.98, 16.58, 18.90, 20.30, 22.22, 23.38, 24.31, 25.39, 25.80 or 26.90+/−0.2 degrees two-theta.

In another aspect, the novel salt of S-apomorphine is used in the production of a solid dosage form, a semi-solid dosage form, or a liquid dosage form in pharmaceutical compositions in a variety of drug delivery systems. In one embodiment, the solid dosage form is selected from a tablet or capsule dosage forms.

In another embodiment, the liquid dosage form is selected from an oral solution, a solution for drop administration or spray administration, e.g., intranasal or pulmonary administration, and parenteral administration, e.g., intramuscular (IM), subcutaneous (SC) or intravenous (IV) administration.

In another aspect, the invention provides for a pharmaceutical composition or dosage form comprising the S-apomorphine hydrochloride hydrate salt.

In some embodiments, the novel hydrochloride hydrate salt of S-apomorphine has improved physicochemical properties and/or modified pharmacokinetics after administration, as compared to crystalline, non-formulated free form of S-apomorphine. Suitable routes of administration include parenteral, enteral, and topical administration, e.g. oral, sublingual, buccal, nasal, pulmonary, e.g., inhaled, transdermal and any other suitable route where the drug is intended for systemic delivery. It can also be administered locally (e.g. topical, ocular) to treat different symptoms that S-apomorphine is prescribed for.

Another aspect of the present invention provides for a method of treatment of a disease or disorder for which S-apomorphine is indicated, e.g., motor neurone disease, amyotrophic lateral sclerosis (ALS), primary lateral sclerosis (PLS), Huntington's disease, Alzheimer's disease, Parkinson's disease, or age-related macular degeneration.

The foregoing and other features and advantages of the invention will become more apparent from the following detailed description, which proceeds with reference to the accompanying drawings. Such description is meant to be illustrative, and not limiting, of the invention. Obvious variants of the disclosed invention in the text, including those described by the drawings and examples will be readily apparent to the person of ordinary skill in the art having the present disclosure, and such variants are considered to be a part of the current invention.

BRIEF DESCRIPTION OF THE DRAWINGS AND TABLES

FIG. 1—TGA pattern of S-apomorphine hydrochloride after vacuum oven drying.

Figure 2:
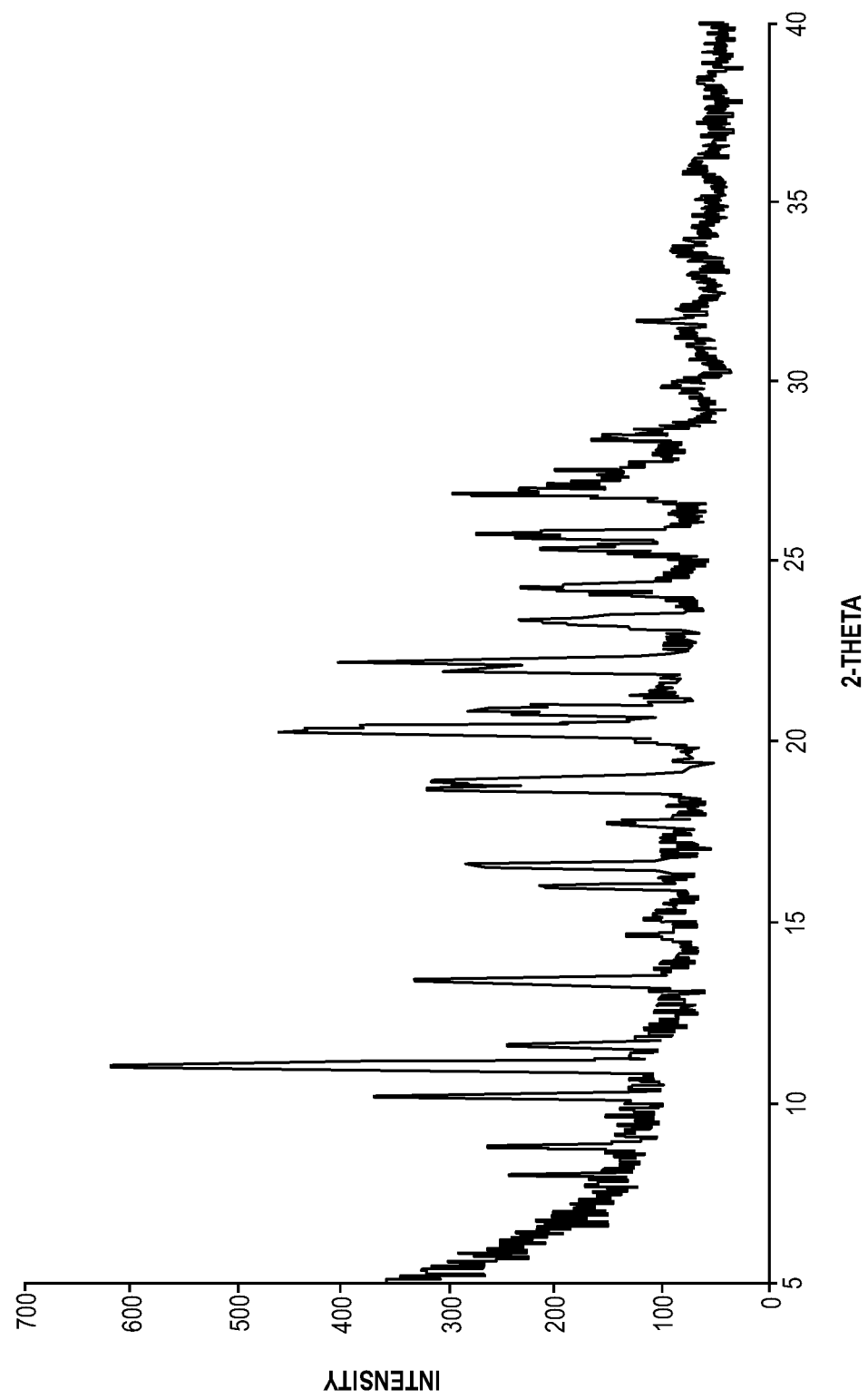

FIG. 2—PXRD pattern of a crystalline form of S-apomorphine hydrochloride hydrate.

Figure 3:
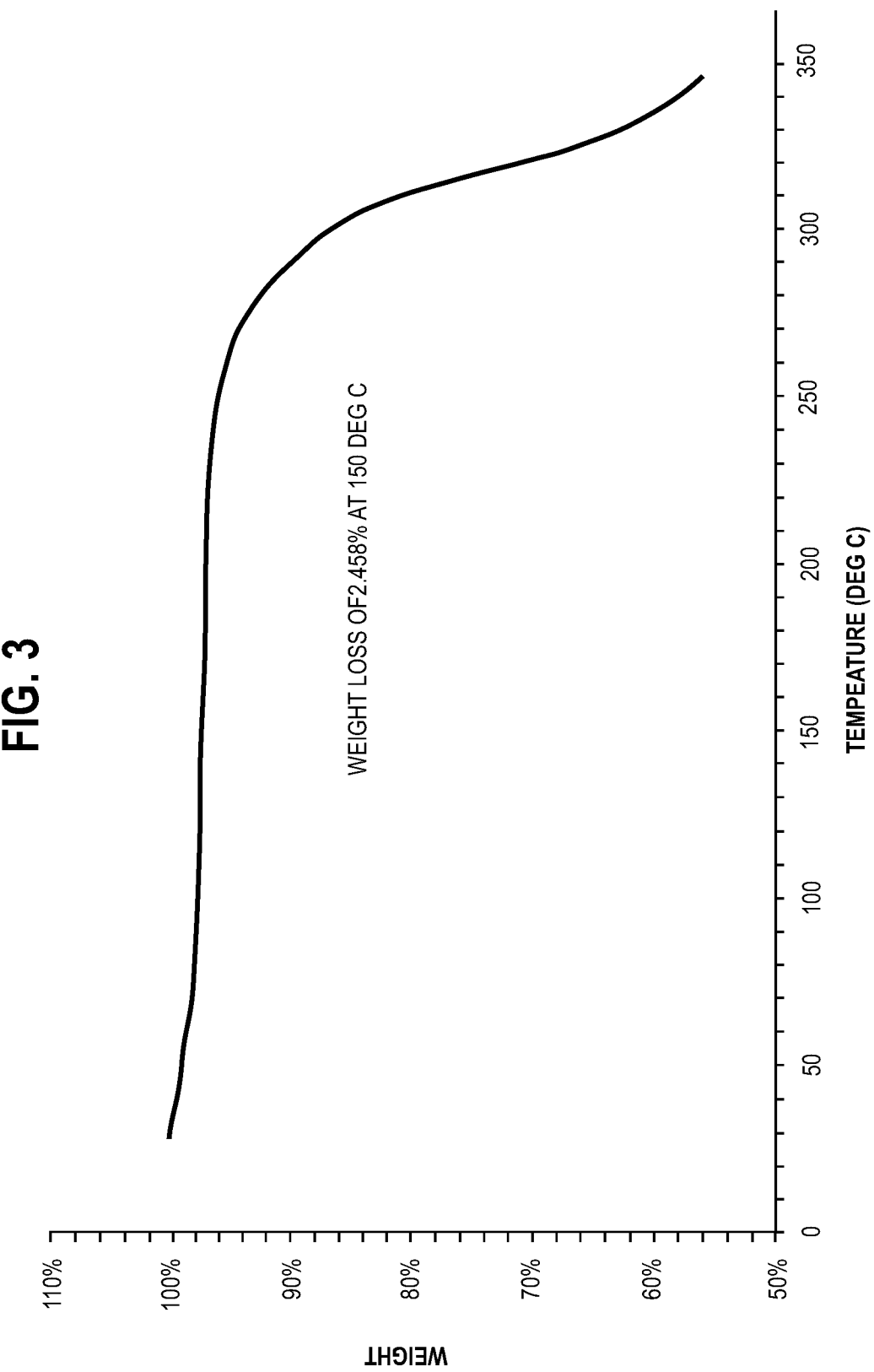

FIG. 3—TGA pattern of a crystalline form of S-apomorphine hydrochloride hydrate.

DETAILED DESCRIPTION

The term 'active pharmaceutical ingredient(s)' or 'S-apomorphine' refers to the substance in a pharmaceutical drug that is biologically active.

As used herein, the terms 'prevent', 'preventing' or 'prevention' means to protect, promote and maintain health and well-being, or to prevent disease, disability, and death.

As used herein, the terms 'treat', 'treating' or 'treatment' means to alleviate, reduce or abrogate one or more symptoms or characteristics of a disease and may be curative, palliative, prophylactic or slow the progression of the disease.

The term 'therapeutically effective amount' means an amount of S-apomorphine, alone or combined with other active ingredients, that will elicit a desired biological or pharmacological response, e.g., effective to prevent, alleviate, or ameliorate symptoms of a disease or disorder; slow, halt or reverse an underlying disease process or progression; partially or fully restore cellular function; or prolong the survival of the subject being treated.

The term 'patient' or 'subject' includes mammals, especially humans. In one embodiment the patient or subject is a human. In another embodiment the patient or subject is a human male. In another embodiment the patient or subject is a human female.

The term 'significant' or 'significantly' is determined by t-test at 0.05 level of significance.

The term 'salt' refers to an ionic compound resulting from the neutralization reaction of an acid and a base, and in the case of a composition of the present invention, whereby one of the ions is S-apomorphine and one of the ions, of an opposite charge, is a coformer, whereby the product is neutral (without a net charge). The term salt includes solvates, including hydrates, of the salt.

The present invention is directed to a novel crystalline S-apomorphine hydrochloride hydrate salt as well as pharmaceutical compositions and dosage forms comprising the same. In some embodiment, the S-apomorphine salt has improved solubility, stability, oral bioavailability, and/or safety profile, compared to crystalline S-apomorphine free-form. The invention further relates to uses of the S-apomorphine hydrochloride hydrate salt.

In one embodiment, the molar ratio of S-apomorphine cation:hydrochloride anion:water is about 1:1:0.3-0.55. In further embodiments, the molar ratio of S-apomorphine cation:hydrochloride anion:water is selected from the group consisting of about: 1:1:0.30-0.4, 1:1:0.30-0.35, 1:1:0.35-0.40 1:1:0.40-0.50, 1:1:0.40-0.45, 1:1:0.45-0.50, 1:1:0.0.41-0.45, 1:1:0.42-0.44, 1:1:0.43, and 1:1:0.50-0.55.

In another embodiment, the S-apomorphine hydrochloride hydrate salt has a water content of about 1.75%-3.2%. In further embodiments, the S-apomorphine hydrochloride hydrate salt has a water content selected from the group consisting of about: 1.2-1.5%, 1.5-1.75%, 1.75%-2.0%, 2.0-2.5%, 2.2-2.8%, 2.3-2.7%, 2.4-2.6%, 2.46%, 2.5%, 2.5-2.75%, 2.75%-3.0%, 3.0-3.15%, and 3.1-3.2%.

In another embodiment, the S-apomorphine hydrochloride hydrate salt is a S-apomorphine hydrochloride hemihydrate salt.

The S-apomorphine hydrochloride hydrate salt may be prepared using known techniques such as dry or solvent-assisted grinding, heating, slurry, sonication, supercritical fluid method or solvent evaporation of their solution in single or mixed solvent systems.

In another embodiment, the S-apomorphine hydrochloride hydrate salt is characterized by a powder X-ray diffraction pattern (Cu X-ray source) comprising a powder X-ray diffraction peak at about 7.99±0.2 degrees 2-theta. In another embodiment, the S-apomorphine hydrochloride hydrate salt is characterized by a powder X-ray diffraction pattern (Cu X-ray source) comprising a powder X-ray diffraction peak at about 8.81±0.2 degrees 2-theta. In another embodiment, the S-apomorphine hydrochloride hydrate salt is characterized by a powder X-ray diffraction pattern (Cu X-ray source) comprising a powder X-ray diffraction peak at about 10.17±0.2 degrees 2-theta. In another embodiment, the S-apomorphine hydrochloride hydrate salt is characterized by a powder X-ray diffraction pattern (Cu X-ray source) comprising a powder X-ray diffraction peak at about 11.00±0.2 degrees 2-theta. In another embodiment, the S-apomorphine hydrochloride hydrate salt is characterized by a powder X-ray diffraction pattern (Cu X-ray source) comprising a powder X-ray diffraction peak at about 11.60±0.2 degrees 2-theta. In another embodiment, the S-apomorphine hydrochloride hydrate salt is characterized by a powder X-ray diffraction pattern (Cu X-ray source) comprising a powder X-ray diffraction peak at about 13.39±0.2 degrees 2-theta. In another embodiment, the S-apomorphine hydrochloride hydrate salt is characterized by a powder X-ray diffraction pattern (Cu X-ray source) comprising a powder X-ray diffraction peak at about 15.98±0.2 degrees 2-theta. In another embodiment, the S-apomorphine hydrochloride hydrate salt is characterized by a powder X-ray diffraction pattern (Cu X-ray source) comprising a powder X-ray diffraction peak at about 16.58±0.2 degrees 2-theta. In another embodiment, the S-apomorphine hydrochloride hydrate salt is characterized by a powder X-ray diffraction pattern (Cu X-ray source) comprising a powder X-ray diffraction peak at about 18.90±0.2 degrees 2-theta. In another embodiment, the S-apomorphine hydrochloride hydrate salt is characterized by a powder X-ray diffraction pattern (Cu X-ray source) comprising a powder X-ray diffraction peak at about 20.30±0.2 degrees 2-theta. In another embodiment, the S-apomorphine hydrochloride hydrate salt is characterized by a powder X-ray diffraction pattern (Cu X-ray source) comprising a powder X-ray diffraction peak at about 22.22±0.2 degrees 2-theta. In another embodiment, the S-apomorphine hydrochloride hydrate salt is characterized by a powder X-ray diffraction pattern (Cu X-ray source) comprising a powder X-ray diffraction peak at about 23.38±0.2 degrees 2-theta. In another embodiment, the S-apomorphine hydrochloride hydrate salt is characterized by a powder X-ray diffraction pattern (Cu X-ray source) comprising a powder X-ray diffraction peak at about 24.31±0.2 degrees 2-theta. In another embodiment, the S-apomorphine hydrochloride hydrate salt is characterized by a powder X-ray diffraction pattern (Cu X-ray source) comprising a powder X-ray diffraction peak at about 25.39±0.2 degrees 2-theta. In another embodiment, the S-apomorphine hydrochloride hydrate salt is characterized by a powder X-ray diffraction pattern (Cu X-ray source) comprising a powder X-ray diffraction peak at about 25.80±0.2 degrees 2-theta. In another embodiment, the S-apomorphine hydrochloride hydrate salt is characterized by a powder X-ray diffraction pattern (Cu X-ray source) comprising a powder X-ray diffraction peak at about 26.90±0.2 degrees 2-theta. In another embodiment, the S-apomorphine hydrochloride hydrate salt is characterized by a powder X-ray diffraction pattern (Cu X-ray source) comprising any two or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any three or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any four or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any five or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any six or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any seven or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any eight or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any nine or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any ten or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any eleven or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any twelve or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction patter (Cu X-ray source)n comprising any thirteen or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any fourteen or more powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising any fifteen or sixteen powder X-ray diffraction peaks selected from the group consisting of: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising powder X-ray diffraction peaks at about 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta. In another embodiment, the S-apomorphine hydrochloride hydrate salt is characterized by a powder X-ray diffraction pattern (Cu X-ray source) comprising powder X-ray diffraction peaks at about 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta.

In another aspect, the novel salt of S-apomorphine is used for the development of a solid dosage form, a semi-solid dosage form, or a liquid dosage form in pharmaceutical compositions in a variety of drug delivery systems. In addition to the salt, such pharmaceutical dosage form may include one or more pharmaceutically acceptable carriers, including, without limitation, binders, fillers, lubricants, emulsifiers, suspending agents, sweeteners, flavorings, preservatives, buffers, wetting agents, disintegrants, effervescent agents and other conventional excipients and additives. Drug delivery routes include, but is not limited to, oral, parenteral, sublingual, buccal, nasal, inhalational, transdermal and any other suitable route where the drug is intended for systemic delivery. It can also be administered locally (e.g. topical, ocular) to treat different symptoms that S-apomorphine is prescribed for.

In one embodiment, the solid dosage form is selected from a tablet or capsule dosage forms.

In another embodiment, the liquid dosage form is selected from an oral solution, a solution for drop administration or spray administration, and parenteral administration.

Another aspect of the present invention provides for a method of prevention and/or treatment of a disease for which S-apomorphine is indicated, e.g., treatment of ALS.

The pharmaceutical compositions of the present invention comprise a therapeutically effective amount S-apomorphine HCl and at least one pharmaceutically acceptable excipient. The term "excipient" refers to a pharmaceutically acceptable, inactive substance used as a carrier for the pharmaceutically active ingredient (S-apomorphine HCl), and includes antiadherents, binders, coatings, disintegrants, fillers, diluents, solvents, flavors, bulkants, colours, glidants, dispersing agents, wetting agents, lubricants, preservatives, sorbents and sweeteners. The choice of excipient(s) will depend on factors such as the particular mode of administration and the nature of the dosage form. Solutions or suspensions used for injection or infusion can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes, including autoinjectors, or multiple dose vials made of glass or plastic.

A pharmaceutical formulation of the present invention may be in any pharmaceutical dosage form. The pharmaceutical formulation may be, for example, a tablet, capsule, nanoparticulate material, e.g., granulated particulate material or a powder. The S-apomorphine HCl may further be used to prepare a liquid pharmaceutical dosage form including a liquid solution, suspension, emulsion or other liquid form. Other dosage forms include a suppository or transdermal preparation or patch. The pharmaceutical formulations generally contain about 1% to about 99% by weight of S-apomorphine HCl and 99% to 1% by weight of a suitable pharmaceutical excipient. In one embodiment, the dosage form is an oral dosage form. In another embodiment, the dosage form is a parenteral dosage form. In another embodiment, the dosage form is an enteral dosage form. In another embodiment, the dosage form is a topical dosage form. In one embodiment, the pharmaceutical dosage form is a unit dose. The term 'unit dose' refers to the amount of S-apomorphine HCl administered to a patient in a single dose.

In some embodiments, a pharmaceutical composition of the present invention is delivered to a subject via a parenteral route, an enteral route, or a topical route.

Examples of parental routes the present invention include, without limitation, any one or more of the following: intraabdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, intracoronary, intracorporus, intracranial, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intraocular, intrasinal, intraspinal, intrasynovial, intratendinous, intratesticular, intrathecal, intrathoracic, intratubular, intratumoral, intratympanic, intrauterine, intravascular, intravenous (bolus or drip), intraventricular, intravesical, and/or subcutaneous.

Enteral routes of administration of the present invention include administration to the gastrointestinal tract via the mouth (oral), stomach (gastric), and rectum (rectal). Gastric administration typically involves the use of a tube through the nasal passage (NG tube) or a tube in the esophagus leading directly to the stomach (PEG tube). Rectal administration typically involves rectal suppositories. Oral administration includes sublingual and buccal administration.

Topical administration includes administration to a body surface, such as skin or mucous membranes, including intranasal and pulmonary administration. Transdermal forms include cream, foam, gel, lotion or ointment. Intranasal and pulmonary forms include liquids and powders, e.g., liquid spray.

The dose may vary depending upon the dosage form employed, sensitivity of the patient, and the route of administration. Dosage and administration are adjusted to provide sufficient levels of the active agent(s) or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy.

In one embodiment, the daily dose of S-apomorphine HCl administered to a patient is selected from: up to 200 mg, 175 mg, 150 mg, 125 mg, 100 mg, 90 mg, 80 mg, 70 mg, 60 mg, 50 mg, 30 mg, 25 mg, 20 mg, 15 mg, 14 mg, 13 mg, 12 mg, 11 mg, 10 mg, 9 mg, 8 mg, 7 mg, 6 mg, 5 mg, 4 mg, 3 mg, or up to 2 mg. In another embodiment, the daily dose is at least 1 mg, 2 mg, 3 mg, 4 mg, 5 mg, 6 mg, 7 mg, 8 mg, 9 mg, 10 mg, 12 mg, 13 mg, 14 mg, 15 mg, 20 mg, 25 mg, 30 mg, 40 mg, 50 mg, 60 mg, 70 mg, 80 mg, 90 mg, 100 mg, 125 mg, 150 mg, 175 mg, or at least 200 mg. In another embodiment, the daily dose is 1-2 mg, 2-4 mg, 1-5 mg, 5-7.5 mg, 7.5-10 mg, 10-15 mg, 10-12.5 mg, 12.5-15 mg, 15-17.7 mg, 17.5-20 mg, 20-25 mg, 20-22.5 mg, 22.5-25 mg, 25-30 mg, 25-27.5 mg, 27.5-30 mg, 30-35 mg, 35-40 mg, 40-45 mg, or 45-50 mg, 50-75 mg, 75-100 mg, 100-125 mg, 125-150 mg, 150-175 mg, 175-200 mg, or more than 200 mg.

In another embodiment, a single dose of S-apomorphine administered to a patient is selected from: 1 mg, 2 mg, 3 mg, 4 mg, 5 mg, 6 mg, 7 mg, 8 mg, 9 mg, 10 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 35 mg, 40 mg, 45 mg, or 50 mg. In another embodiment, a single dose of S-apomorphine administered to a patient is selected from: 1-2 mg, 2-4 mg, 1-5 mg, 5-7.5 mg, 7.5-10 mg, 10-15 mg, 10-12.5 mg, 12.5-15 mg, 15-17.7 mg, 17.5-20 mg, 20-25 mg, 20-22.5 mg, 22.5-25 mg, 25-30 mg, 25-27.5 mg, 27.5-30 mg, 30-35 mg, 35-40 mg, 40-45 mg, 45-50 mg, 50-75 mg, 75-100 mg, 100-125 mg, 125-150 mg, 150-175 mg, 175-200 mg, or more than 200 mg. In one embodiment, the single dose is administered by a route selected from any one of: oral, buccal, or sublingual administration. In another embodiment, said single dose is administered by injection, e.g., subcutaneous, intramuscular, or intravenous. In another embodiment, said single dose is administered by inhalation or intranasal administration.

As a non-limited example, the dose of S-apomorphine administered by subcutaneous injection may be about 3 to 50 mg per day to be administered in divided doses. A single dose of S-apomorphine administered by subcutaneous injection may be about 1-6 mg, preferably about 1-4 mg, 1-3 mg, or 2 mg. Subcutaneous infusion may be preferable in those patients requiring division of injections into more than 10 doses daily. The continuous subcutaneous infusion dose may be 1 mg/hour daily and is generally increased according to response up to 4 mg/hour.

The fine particle dose of S-apomorphine administered by pulmonary administration, e.g., inhalation using a pressurized metered dose inhaler (pMDI), dry powder inhaler (DPI), soft-mist inhaler, nebulizer, or other device, may be in the range of about, 0.5-15 mg, preferably about 0.5-8 mg or 2-6 mg. The Nominal Dose (ND), i.e., the amount of drug metered in the receptacle (also known as the Metered Dose), of S-apomorphine administered by pulmonary administration may be, for example, in the range of 0.5-15 mg, 3-10 mg, 10-15 mg, 10-12.5 mg, 12.5-15 mg, 15-17.7 mg, 17.5-20 mg, 20-25 mg, 20-22.5 mg, 22.5-25 mg, 25-30 mg, 25-27.5 mg, 27.5-30 mg, 30-35 mg, 35-40 mg, 40-45 mg, or 45-50 mg.

Long-acting pharmaceutical compositions may be administered, 1, 2, 3, 4, 5, 6, 7, 8, 9, 10 or more than 10 times daily (preferably <10 times per day), every other day, every 3 to 4 days, every week, or once every two weeks depending on half-life and clearance rate of the particular formulation.

EXAMPLE

The following examples illustrate the invention without intending to limit the scope of the invention.

S-apomorphine hydrochloride hydrate salt was characterized by its powder X-ray diffraction (PXRD) pattern and thermogravimetric analysis (TGA) pattern disclosed herein.

Solid Phase Characterization

Analytical techniques used to observe the crystalline forms include PXRD and TGA analyses. The particular methodology used in such analytical techniques should be viewed as illustrative, and not limiting in the context of data collection. For example, the particular instrumentation used to collect data may vary; routine operator error or calibration standards may vary; sample preparation method may vary (for example, the use of the KBr disk or Nujol mull technique for FTIR analysis).

PXRD: the sample was examined using D8 advance X-ray diffractometer (Bruker). The diffractometer was equipped with LynxEye detector. Tube element was Cu, the wavelength is 1.54184 Å, the tube voltage and current were 40 KV and 40 mA, respectively. The sample was scanned from 3 to 40 degree-2θ at a step of 0.02 degree-2θ. Scan speed was 0.3 s/step.

TGA: TGA analysis was performed on a TA Instrument TGA Q500 (TA Instruments, US). The sample was placed in an open tarred aluminum pan, automatically weighed, and inserted into the TGA furnace. The temperature range was from room temperature to approximately 350° C., at a rate of 10° C./min. Data are reported as percentage weight decrease.

S-apomorphine was provided by Santa Cruz Biotechnology as a mixed hydrated form of S-apomorphine hydrochloride (batch #: D2017). The water content of this material was determined to be 1.1%, as reported in the certificate of analysis.

The received S-apomorphine was dried in the vacuum oven at 50° C. for 2 hours and TGA characterization was performed immediately after vacuum oven drying (FIG. 1). The dried material was then stored at ambient conditions for 6 hours till the stable crystal form of S-apomorphine hydrochloride hydrate was formed. The hydrate was characterized by PXRD analysis (FIG. 2). Table 1 below lists representative peaks from the PXRD pattern of S-apomorphine hydrochloride hydrate. Representative peaks in Table 1 or a subset of those peaks, as well as the peaks shown in FIG. 1 or a subset of those peaks, can be used to characterize S-apomorphine hydrochloride hydrate of the invention.

The hydrate was also characterized by TGA analysis. FIG. 3 shows a TGA pattern of S-apomorphine hydrochloride hydrate. The data shown in FIG. 3 can be used to characterize S-apomorphine hydrochloride hydrate of the invention.

TABLE 1

| PXRD Peaks (° 2-theta ± 0.2° 2-theta) | Intensity % |
|---|---|
| 7.99 | 38.8 |
| 8.81 | 42.1 |
| 10.17 | 59.5 |
| 11.00 | 100 |
| 11.60 | 39.5 |
| 13.39 | 53.6 |

TABLE 1-continued

| PXRD Peaks (° 2-theta ± 0.2° 2-theta) | Intensity % |
| --- | --- |
| 15.98 | 34.5 |
| 16.58 | 45.6 |
| 18.90 | 50.6 |
| 20.30 | 70.2 |
| 22.22 | 65.2 |
| 23.38 | 37.4 |
| 24.31 | 37.4 |
| 25.39 | 34.3 |
| 25.80 | 44.0 |
| 26.90 | 47.7 |

I claim:

1. An S-apomorphine hydrochloride hydrate salt, wherein the S-apomorphine hydrochloride hydrate salt is characterized by a powder X-ray diffraction pattern (Cu X-ray source) comprising peaks at about 10.17, 11.00, 13.39, 18.90, 20.30, and 22.22±0.2 degrees 2-theta.

2. The S-apomorphine hydrochloride hydrate salt of claim 1, wherein the powder X-ray diffraction pattern (Cu X-ray source) further comprises at least one peak selected from the group consisting of about: 7.99, 8.81, 11.60, 15.98, 16.58, 23.38, 24.31, 25.39, 25.80 and 26.90±0.2 degrees 2-theta.

3. The S-apomorphine hydrochloride hydrate salt of claim 2, wherein the S-apomorphine hydrochloride hydrate salt is characterized by a powder X-ray diffraction pattern (Cu X-ray source) comprising at least six, at least seven, at least eight, at least nine, at least ten, at least eleven, at least twelve, at least thirteen, at least fourteen, at least fifteen, or all sixteen, powder X-ray diffraction peaks selected from the group consisting of about: 7.99, 8.81, 10.17, 11.00, 11.60, 13.39, 15.98, 16.58, 18.90, 20.30, 22.22, 23.38, 24.31, 25.39, 25.80 and 26.90±0.2 degrees 2-theta.

4. The S-apomorphine hydrochloride hydrate salt of claim 1, wherein the S-apomorphine hydrochloride hydrate salt is characterized by a powder X-ray diffraction pattern (Cu X-ray source) substantially as depicted in FIG. 2.

5. The S-apomorphine hydrochloride hydrate salt of claim 1, wherein the salt is a S-apomorphine hydrochloride hemihydrate salt.

6. The S apomorphine hydrochloride hydrate salt of claim 1, wherein the salt has a molar ratio of S-apomorphine cation:hydrochloride anion:water that is selected from the group consisting of about: 1:1:0.30-0.4, 1:1:0.30-0.35, 1:1: 0.35-0.40 1:1:0.40-0.50, 1:1:0.40-0.45, 1:1:0.45-0.50, 1:1: 0.0.41-0.45, 1:1:0.42-0.44, 1:1:0.43, and 1:1:0.50-0.55.

7. The S-apomorphine hydrochloride hydrate salt of claim 1, wherein the salt has a molar ratio of S-apomorphine cation:hydrochloride anion:water of about 1:1:0.30-0.55.

8. The S-apomorphine hydrochloride hydrate salt of claim 1, wherein the S-apomorphine hydrochloride hydrate salt is characterized by thermogravimetric analysis, showing a water content selected from the group consisting of about: 1.2-1.5%, 1.5-1.75%, 1.75%-3.2%, 1.75%-2.0%, 2.0-2.5%, 2.2-2.8%, 2.3-2.7%, 2.4-2.6%, 2.46%, 2.5%, 2.5-2.75%, 2.75%-3.0%, 3.0-3.15%, and 3.1-3.2%.

9. The S-apomorphine hydrochloride hydrate salt of claim 8, wherein the salt has a water content of about 1.75-3.2%.

10. A pharmaceutical composition comprising the S-apomorphine hydrochloride hydrate salt of claim 1 and a pharmaceutically acceptable excipient.

11. The pharmaceutical composition of claim 10, wherein the pharmaceutical composition is for parenteral, enteral, or topical administration.

12. The pharmaceutical composition of claim 11, wherein the pharmaceutical composition is for intramuscular, intravascular, intravenous, subcutaneous, oral, sublingual, buccal, intranasal, transdermal, or pulmonary administration.

13. The pharmaceutical composition of claim 10, wherein the pharmaceutical composition is a solid dosage form.

14. The pharmaceutical composition of claim 13, wherein the pharmaceutical composition is a solid dosage form for reconstitution in a liquid medium.

15. The pharmaceutical composition of claim 10, wherein the pharmaceutical composition is a unit dose.

16. The pharmaceutical composition of claim 15, wherein the unit dose is a tablet or capsule.

17. A method for treating a disease or disorder for which S-apomorphine is indicated, said method comprising the step of administering to a patient in need thereof a therapeutically effective amount of the pharmaceutical composition of claim 10.

18. The method of claim 17, wherein said disease or disorder is selected from the group consisting of: motor neuron disease, amyotrophic lateral sclerosis (ALS), primary lateral sclerosis (PLS), Huntington's disease, Alzheimer's disease, Parkinson's disease, and age-related macular degeneration.

* * * * *